(12) United States Patent
Rogers et al.

(10) Patent No.: US 7,182,940 B1
(45) Date of Patent: Feb. 27, 2007

(54) SHEA BUTTER ESTERS

(75) Inventors: Steven Rogers, Yardley, PA (US); Anthony O'Lenick, Jr., Dacula, GA (US)

(73) Assignee: Rutherford Chemicals, LLC, Bayonne, NJ (US)

( * ) Notice: Subject to any disclaimer, the term of this patent is extended or adjusted under 35 U.S.C. 154(b) by 0 days.

(21) Appl. No.: 11/347,262

(22) Filed: Feb. 6, 2006

(51) Int. Cl.
*A61K 7/06* (2006.01)
*A61K 7/075* (2006.01)
*A61K 7/08* (2006.01)
*C07C 51/50* (2006.01)

(52) U.S. Cl. .................. 424/70.1; 424/70.31; 554/2

(58) Field of Classification Search .................. 554/2; 424/70.1, 70.31
See application file for complete search history.

(56) References Cited

U.S. PATENT DOCUMENTS

2005/0233015 A1* 10/2005 Norberg et al. ............. 424/769

* cited by examiner

*Primary Examiner*—Deborah D. Carr

(57) ABSTRACT

Novel esters prepared by the reaction of shea butter, preferably mild-processed shea butter (MPSB), and fatty alcohol. Materials of the present invention are useful as cosmetic and personal care ingredients, allowing for the delivery of highly desirable active ingredients present in shea butter, including natural antioxidants, in an oil-soluble, emollient material that is substantive to the skin and hair.

18 Claims, No Drawings

SHEA BUTTER ESTERS

CROSS-REFERENCE TO RELATED APPLICATIONS

Not applicable.

STATEMENT REGARDING FEDERALLY-SPONSORED RESEARCH OR DEVELOPMENT

Not applicable.

FIELD OF THE INVENTION

The present invention relates to novel shea butter esters, prepared by the reaction of a fatty alcohol and shea butter, preferably mild-processed shea butter (MPSB). These compounds are useful as cosmetic and personal care ingredients, allowing for the delivery of highly desirable active ingredients present in shea butter, including natural antioxidants, in an oil-soluble, emollient material that is substantive to the skin and hair.

BACKGROUND OF THE INVENTION

Fatty esters are a class of oil-phase materials that have been widely used for many years in the cosmetic and personal care industries. Often, because a primary use of these compounds is as an emollient, they are referred to as "mono-functional." Related to this property is the ability to help reduce transepidermal water loss, enhance skin barrier function and improve skin hydration. In contrast, the fatty esters of the present invention are multi-functional—they provide emolliency (and its associated benefits) while at the same time effectively delivering antioxidants to the hair and skin. The latter property is attributable to the high concentration of antioxidants in the unsaponifiable fraction of shea butter, particularly MPSB, that is produced and maintained through the use of mild-processing steps, both in the preparation of the starting material (mild-processed shea butter) and its subsequent processing into the claimed MPSB ester derivatives.

Shea Butter is a butter extracted from the kernel of *Butrospermum parkii*. This plant, also referred to as *Vitellaria paradoxa*, is native to Africa. The term butter describes a material that is a solid at room temperature, but melts at about 40° C. Chemically, the butter is a triglyceride conforming to the following structure

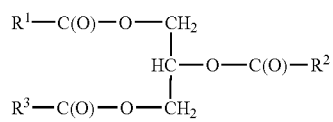

wherein $R^1$, $R^2$ and $R^3$ each have one of the following compositions:

| R Group | Common Name | Range (%) | Typical (%) |
|---|---|---|---|
| $C_{11}H_{23}$ | Lauryl | 0.1–2.0 | 0.2 |
| $C_{13}H_{27}$ | Myristyl | 0.5–2.0 | 1.0 |
| $C_{15}H_{31}$ | Cetyl | 2.0–6.0 | 4.0 |

-continued

| R Group | Common Name | Range (%) | Typical (%) |
|---|---|---|---|
| $C_{17}H_{35}$ | Stearyl | 25.0–50.0 | 35.0 |
| $C_{17}H_{33}$ | Oleyl | 40.0–60.0 | 59.0 |
| $C_{17}H_{31}$ | Linoleyl | 0.5–1.0 | 0.8 |

The average composition of $R^2$ is different than $R^1$ and $R^3$, the latter two being similar. The $R^2$ moiety contains predominantly the unsaturated $C_{18}$ group (oleyl) while $R^1$ and $R^3$ contain predominantly the saturated $C_{18}$ group (stearyl). Differences between internal ($R^2$) and terminal ($R^1$, $R^3$) substitution are seen in natural products but not in synthetic molecules produced in the laboratory.

The high levels of stearyl and oleyl groups make shea butter and its ester derivatives of particular interest in the personal care industry. While other raw materials used in personal care products have these species, the compounds of the present invention have significantly high concentrations of unsaponifiables, which posses highly desired antioxidant, ultra-violet radiation protection, and free-radical scavenging properties. MPSB of the present invention typically contains from about 5% to about 15% by weight of unsaponifiables. In contrast, other butters commonly used in personal care products have less than 2% unsaponifiables. For example, coca butter (from *Theobroma cacao*) averages 0.4% unsaponifiables and Illipe butter (from *Shorea stenoptera*) averages 1.1%.

The novel shea butter esters of the present invention are produced by reacting shea butter, preferably MPSB, preferably under specific conditions with fatty alcohols. By "mild processed" is meant processes that do not remove or otherwise diminish the amount or potency of active ingredients, particularly highly desired unsaponifiables. In one aspect of the present invention, mild processing is employed both at the time of harvesting and initial extraction and during subsequent preparation of derivatives. These mild processes result in materials containing unexpectedly high amounts unsaponifiables, notably antioxidants.

Fatty alcohols are widely-used in formulating cosmetic and personal care products, typically as emollients, emulsifiers and co-emulsifiers. They are higher molecular weigh non-volatile alcohols produced from natural fats and oils by reduction of the carboxylic acid group on a fatty acid to hydroxyl. Fatty alcohols prepared from naturally-occurring fatty acids normally contain an even number of carbon atoms. Synthetic fatty alcohols with equivalent physico-chemical properties to naturally-derived products are also commercially available.

Fatty alcohols serve to prevent transepidermal water loss and can impart a smooth, velvety feel to the skin and are key ingredients in many shampoos and cleansing surfactants. As chemical intermediates, the primary uses of fatty alcohols include esterification, ethoxylation and sulfation to produce, among other materials, fatty sulfate salts and alcohol ethoxylates.

U.S. Pat. No. 5,646,321 teaches the reaction of a Guerbet alcohol with meadowfoam oil as a triglyceride, as meadow-foam methyl ester (the product of reaction with methanol) or as meadowfoam fatty acid to produce fatty esters that, because of the specific alkyl distribution of meadowfoam oil, are liquid at high temperatures and do not exhibit rancidity (e.g., resulting from the oxidation of a double carbon bond to form malodorous, bad-tasting, aldehydic compounds). The esters described in the '321 patent do not possess the desirable unsaponifiable fractions, and with them antioxidant properties, of the compounds of the present invention.

SUMMARY OF THE INVENTION

The compounds of the present invention are mild-processed shea butter esters produced by reacting shea butter with fatty alcohols. In a preferred aspect of the present invention, mild-processing is employed both at the time of harvesting and initial extraction (creating mild-processed shea butter) and during subsequent preparation of shea butter ester derivatives. The novel compounds of the present invention are rich in unsaponifiables, including antioxidants.

DETAILED DESCRIPTION OF THE INVENTION

The compounds of the present invention are a novel class of esters produced by reacting shea butter with a fatty alcohol. Preferably, the shea butter is mild-processed and is reacted with a fatty alcohol under mild processing conditions. The novel ester compounds of the present invention are rich in unsaponifiables, including antioxidants and free-radical scavengers.

Shea butter esters of the present invention conform to the following structure:

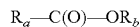

wherein
(i) $R_a$ is derived from shea butter and comprises
from about 0.1 to about 2.0% by weight $C_{11}H_{23}$;
from about 0.5 to about 2.0% by weight $C_{13}H_{27}$;
from about 2.0 to about 6.0% by weight $C_{15}H_{31}$;
from about 25 to about 50% by weight $C_{17}H_{35}$; from about 40.0 to about 60.0% by weight $C_{17}H_{33}$; and
(ii) $R_b$ is $CH_3$—$(CH_2)_n$, wherein n is an integer ranging from 7 to 21.

Another aspect of the present invention is a process for delivering antioxidants to the skin and hair by applying thereto a finished topical product comprising an effective concentration of the above-described shea butter ester. In a preferred embodiment, the effective concentration of shea butter ester is from about 0.1% to about 15.0% by weight of the finished product. By "finished topical product" is meant a cream, lotion, gel, foam, ointment, paste, emulsion, suspension, dispersion, solution, or similar topically-applied carrier or delivery system known to those of skill in the art.

Shea Butter

Shea butter can be prepared by standard extraction techniques known to those of skill in the art. For example, U.S. Pat. No. 6,552,208, the disclosure of which is incorporated herein by reference, describes several methods for processing shea butter. Suitable extraction vehicles may include, but are not limited to, ethanol, methanol, ethyl acetate, acetone, chloroform and water, or any other solvent and water.

In a preferred aspect of the present invention, shea butter is mild-processed; it is extracted using a hydrocarbon-free solvent system, and its ester derivatives are made under mild processing conditions. At the time of harvesting and initial extraction, ground-up kernels are boiled in water under mild conditions as described in the example below. The oil phase is then separated from the water phase by decanting. This process provides a yellow solid wax rich in unsaponifiables. By wax is meant a material obtained by boiling in water under ambient conditions, decanted and filtered.

The mild processing of the present invention may be contrasted with separation using solvents and high temperature treatment with high pressure steam. While the latter processes result in what some may describe as a "more pure" triglyceride, unsaponifiables, and the benefits derived therefrom, are lost. Vacuum distillation which strips off the desirable components is also to be avoided in processing MPSB of the present invention. By processing shea butter under mild conditions, materials comprising from about 5% to about 15% by weight of unsaponifiables can be produced.

Sterols comprise about 20% of the unsaponifiables in shea butter. More particularly, the sterols comprise: cholesterol (from about 1% to about 3%); alpha-spinasterol (from about 1% to about 4%); delta-7-stigmasterol (from about 40% to about 44%); delta-7-avenasterol (from about 38% to about 41%). The remaining constituents of the unsaponifiables (about 80%) include other highly desirable active compounds including tocopherol, karitin, cinamic acid esters, alpha and beta amyrin and phenolics.

Phenolic compounds are natural products composed of one or more aromatic benzene rings with one or more hydroxyl group. They are a class of natural products that possess antioxidant and free radical scavenging properties. Among the phenolics in the unsaponifiables of mild-processed shea butter include gallic acid, gallocatchin, catechin, epigallocatechin gallate, epicatechin, gallocatechin gallate, gallocatechin gallate and quercetin.

Fatty Alcohols

Fatty alcohols suitable for use in the present invention may be derived from natural fats and oils or, alternatively, from synthetic routes. Preferred fatty alcohols are straight chain primary alcohols conforming to the formula: $R^2$=$CH_3$—$(CH_2)_n$—$OH$, where n ranges from 7 to 22. Representative fatty alcohols suitable for use in the present invention are listed below:

| Example | N value | Common Name |
| --- | --- | --- |
| 1 | 7 | Octanol |
| 2 | 9 | Decanol |
| 3 | 11 | Lauryl alcohol |
| 4 | 13 | Myristyl alcohol |
| 5 | 15 | Palmityl alcohol; Cetyl alcohol |
| 6 | 17 | Stearyl alcohol |
| 7 | 21 | Behenyl alcohol |

Particularly preferred fatty alcohols for use in the present invention are oleyl, behenyl and lauryl.

The following examples are further illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

EXAMPLES

The starting MPSB is made according to following procedure: 200.0 grams of the nut form the Shea Butter tree are cracked into small pieces and placed into a one-liter vat of water. The water is then heated to 1001° C. As the temperature increases, an oil phase develops on the surface of the water. The temperature is held for about 2 hours, after which the oil is decanted and passed through filter paper. The resulting butter is mild-processed shea butter according to the present invention. It is rich in unsaponifiables (from about 7% to about 15% by weight) and may be used in making the MPSB esters of the present invention.

Fatty alcohols as described in Examples 1–7 are reacted with MPSB as follows: To 145.0 grams of the mild-processed shea butter are added the specified number of grams of fatty alcohols in Examples 8–14. Using a reflux condenser, the temperature of the mass is raised to 180° C.–190° C. The mass is held within this temperature range for 16 hours. Nothing is distilled off during this time, and the reaction mass becomes hazy. The reaction mass is cooled, glycerin separates off and is removed from the bottom. The products of Example 8–14 may be used in formulating finished cosmetic and personal care products without additional purification.

| Example | Fatty Alcohol Example | Grams |
|---|---|---|
| 8 | 1 | 65.0 |
| 9 | 2 | 79.0 |
| 10 | 3 | 93.0 |
| 11 | 4 | 107.0 |
| 12 | 5 | 221.0 |
| 13 | 6 | 235.0 |
| 14 | 7 | 163.0 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A process for delivering antioxidants to the hair and skin by applying thereto a finished topical product comprising an effective concentration of a shea ester conforming to the structure $R_a$—C(O)—$OR_b$ wherein
    (i) $R_a$ is derived from shea butter and comprises
        from about 0.1 to about 2.0% by weight $C_{11}H_{23}$;
        from about 0.5 to about 2.0% by weight $C_{13}H_{27}$;
        from about 2.0 to about 6.0% by weight $C_{15}H_{31}$;
        from about 25 to about 50% by weight $C_{17}H_{35}$;
        from about 40.0 to about 60.0% by weight $C_{17}H_{33}$; and
    (ii) $R_b$ is $CH_3$—$(CH_2)_n$, wherein n is an integer ranging from 7 to 21.

2. A process for delivering antioxidants to the hair and skin by applying thereto a finished topical product comprising an effective concentration of a shea butter ester of claim 1 wherein n is 7.

3. A process for delivering antioxidants to the hair and skin by applying thereto a finished topical product comprising an effective concentration of a shea butter ester of claim 1 wherein n is 9.

4. A process for delivering antioxidants to the hair and skin by applying thereto a finished topical product comprising an effective concentration of a shea butter ester of claim 1 wherein n is 11.

5. A process for delivering antioxidants to the hair and skin by applying thereto a finished topical product comprising an effective concentration of a shea butter ester of claim 1 wherein n is 13.

6. A process for delivering antioxidants to the hair and skin by applying thereto a finished topical product comprising an effective concentration of a shea butter ester of claim 1 wherein n is 15.

7. A process for delivering antioxidants to the hair and skin by applying thereto a finished topical product comprising an effective concentration of a shea butter ester of claim 1 wherein n is 17.

8. A process for delivering antioxidants to the hair and skin by applying thereto a finished topical product comprising an effective concentration of a shea butter ester of claim 1 wherein n is 21.

9. A process of claim 1 where the shea butter is mild-processed.

10. A shea butter ester conforming to the following structure:

$$R_a\text{—C(O)—}OR_b$$

wherein
    (i) $R_a$ is derived from shea butter and comprises
        from about 0.1 to about 2.0% by weight $C_{11}H_{23}$;
        from about 0.5 to about 2.0% by weight $C_{13}H_{27}$;
        from about 2.0 to about 6.0% by weight $C_{15}H_{31}$;
        from about 25 to about 50% by weight $C_{17}H_{35}$;
        from about 40.0 to about 60.0% by weight $C_{17}H_{33}$; and
    (ii) $R_b$ is $CH_3$—$(CH_2)_n$, wherein n is an integer ranging from 7 to 21.

11. A shea butter ester of claim 10 wherein n is 7.
12. A shea butter ester of claim 10 wherein n is 9.
13. A shea butter ester of claim 10 wherein n is 11.
14. A shea butter ester of claim 10 wherein n is 13.
15. A shea butter ester of claim 10 wherein n is 15.
16. A shea butter ester of claim 10 wherein n is 17.
17. A shea butter ester of claim 10 wherein n is 21.
18. A shea butter ester of claim 10 where the shea butter is mild-processed.

* * * * *